United States Patent [19]
Akutsu et al.

[11] Patent Number: 5,042,915
[45] Date of Patent: * Aug. 27, 1991

[54] LIGHT SOURCE APPARATUS FOR AN ENDOSCOPE

[75] Inventors: Hiromichi Akutsu; Sugao Hosoi, both of Ohtawara, Japan

[73] Assignee: Kabushiki Kaisha Toshiba, Kawasaki, Japan

[*] Notice: The portion of the term of this patent subsequent to May 30, 2006 has been disclaimed.

[21] Appl. No.: 147,485

[22] Filed: Jan. 25, 1988

[30] Foreign Application Priority Data

Jan. 26, 1987 [JP] Japan .................. 62-13994

[51] Int. Cl.$^5$ .................. G02B 26/02; F21V 21/26; A61B 1/00; G01J 1/32
[52] U.S. Cl. .................. 359/230; 128/4; 128/5; 128/6; 128/7; 128/8; 128/9; 362/282; 358/98; 250/205; 359/234; 359/290
[58] Field of Search ........... 350/271, 270, 269, 272, 350/362, 359, 360; 128/4, 5-9; 250/205; 362/277, 282; 358/98

[56] References Cited

U.S. PATENT DOCUMENTS

| 1,686,525 | 10/1928 | House | 350/272 |
|---|---|---|---|
| 2,995,797 | 8/1961 | Nieuwenhauen | 350/272 |
| 3,504,962 | 4/1970 | Shanley | 350/272 |
| 4,128,307 | 12/1978 | Badertscher et al. | 350/263 |
| 4,234,245 | 11/1980 | Toda et al. | 350/269 |
| 4,313,650 | 2/1982 | Ward et al. | 350/263 |
| 4,407,272 | 10/1983 | Yamaguchi | 128/6 |
| 4,425,599 | 1/1984 | Rieder et al. | 362/277 |
| 4,444,462 | 4/1984 | Ono et al. | 128/6 X |
| 4,625,236 | 11/1986 | Fujimori et al. | 358/98 |
| 4,710,807 | 12/1987 | Chikama | 358/98 |
| 4,729,018 | 3/1988 | Watanabe et al. | 362/282 X |
| 4,834,071 | 5/1989 | Hosoi et al. | 128/6 |

FOREIGN PATENT DOCUMENTS

| 2060090 | 5/1972 | Fed. Rep. of Germany | 350/269 |
|---|---|---|---|
| 2836861 | 3/1979 | Fed. Rep. of Germany | 350/272 |

OTHER PUBLICATIONS

Naish, "An Electromechanical Optical Shutter", *J. Phys. E: Sci Instrum.*, vol. 12, No. 8, Aug. 1979, pp. 678-679.

*Primary Examiner*—Eugene R. Laroche
*Assistant Examiner*—Michael B. Shingleton
*Attorney, Agent, or Firm*—Foley & Lardner

[57] ABSTRACT

A light source apparatus comprises a light source; a lens for collecting light from the light source; a light guide for receiving the light collected by the lens; and an adjusting device disposed between the light source and the lens and adjusting the quantity of light guided to the light guide so as not to change the light distributing characteristics by a throttled amount of the light quantity.

7 Claims, 7 Drawing Sheets

LIGHT SOURCE APPARATUS FOR AN ENDOSCOPE

The present invention relates to an improvement of a light source apparatus especially in an endoscope for medical care, and in particular, to a light source apparatus which can adjust the illuminating intensity of an illuminated body without preventing light distribution characteristics of the illuminating light.

BACKGROUND OF THE INVENTION

An endoscope is widely used to examine and care portions of a human's body such as duodenum, rectum, large intestine, oesophagus, ears, nose, and urinary bladder.

An electronic endoscope has been recently constructed as follows. Namely, the electronic endoscope comprises, in the front to back direction thereof, an end tip portion for disposing therein a solid image pick-up element (the CCD in the following description) and an optical system for observing a body, a bent portion moved in the upward, downward, right and left directions by the operation of an operator, a guide portion for disposing therein a light guide, a signal line, and a scope portion composed of a hand operating portion, etc. The light from a light source lamp is collected by a collecting mirror and a condenser lens, and is then guided to the light guide composed of optical fibers.

When the quantity of light transmitted to the light guide is too large, halation or blooming occurs to an observed region of the observed body provided by the CCD. When the quantity of light is too small, it is difficult to sufficiently secure the visual field. Accordingly, in the operation of the endoscope, it is necessary to suitably control the quantity of light transmitted to the light guide from the light source apparatus.

In the conventional light source apparatus of the endoscope, a control apparatus illustrated in FIGS. 1A, 1B, 2A and 2B is used as a means for controlling the illuminating intensity.

Namely, in a conventional apparatus shown in FIGS. 1A and 1B, two light interrupting plates A and B are disposed between a condenser lens 3 and a rear end surface 42 of a light guide 4, and are slid in the direction of arrow a with respect to a light flux 44, thereby adjusting the quantity of the incident light irradiated to the light guide 4.

In a conventional apparatus shown in FIGS. 2A and 2B, a light interrupting plate C having a generally Y shape is disposed between the condenser lens 3 and the rear end surface 42 of the light guide 4, and is slid in the direction of arrow b with respect to the light flux 44, thereby adjusting the quantity of the incident light irradiated to the light guide 4.

In the above-mentioned conventional apparatuses shown in FIGS. 1A, 1B, 2A and 2B, the light quantity is adjusted by reducing the collected light flux from the peripheral portion thereof between the condenser lens 3 and the light guide 4 using the light interrupting plates A, B and C. Accordingly, although it is possible to control the illuminating intensity by the nature of the light guide by which light is irradiated only in the same direction as the incident angle, the light distributing characteristics or the intensity distribution of the light irradiated to the illuminated body from the other end of the light guide is changed in accordance with the reduction of the light flux so that a suitable light quantity cannot be obtained in some portions in the visually observed field.

SUMMARY OF THE INVENTION

To overcome the problems of the conventional light source apparatus of an endoscope mentioned above, an object of the present invention is to provide a light source apparatus which can adjust the illuminating intensity of light irradiated to an illuminated body without preventing the light distributing characteristics of the illuminated light.

With this object in view, the present invention resides in a light source apparatus comprising a light source, a condenser lens for collecting light from the light source, and a light guide for guiding the light collected by the condenser lens to an end tip of the endoscope, etc., said light source apparatus being characterized in that a means adjusting the light quantity and provided with a plurality of throttle blades opened and closed with respect to each other is disposed between the light source and the condenser lens.

In the light source apparatus of the endoscope in the present invention, the adjusting means for adjusting the light quantity is composed of the plurality of throttle blades disposed in parallel to each other and opened and closed with respect to each other, and is disposed between the light source and the condenser lens. In this apparatus, a motor for moving the blades is driven by a signal from a motor drive circuit to adjust the open and closed angles of the throttle blades with respect to each other so that the illuminating intensity is easily adjusted.

When the light quantity is adjusted by the throttle blades in the light source apparatus of the endoscope in the present invention, the light flux between the light source and the condenser lens is divided into a plurality of stripes, and the respective striped light are simultaneously adjusted at the same ratio in light intensity to uniformly interrupt the quantity of light transmitted to the entire sectional region of the light guide so that the light distributing characteristics of the light irradiated to the observed body are not prevented.

Accordingly, in the light source apparatus of the endoscope in the present invention, the light intensity or brightness of the observed body can be adjusted without preventing the light distributing characteristics, thereby greatly improving the observation accuracy of the observed body.

BRIEF DESCRIPTION OF THE DRAWINGS

The present invention will be more apparent from the following description of the preferred embodiments thereof in conjunction with the accompanying drawings in which:

FIGS. 1A, 1B, 2A and 2B are respectively views showing devices for adjusting light quantity in conventional light source apparatuses of an endoscope in which FIGS. 1A and 2A are front views, and FIGS. 1B and 2B are side views;

DETAILED DESCRIPTION OF THE PREFERRED EMBODIMENTS

The preferred embodiments of a light source apparatus of an endoscope in the present invention will now be described in detail in conjunction with the accompanying drawings.

Figure 1A:
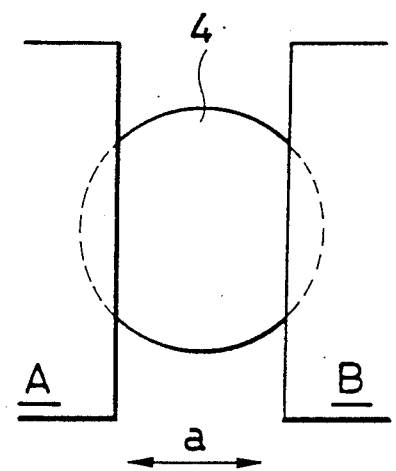
Figure 1B:
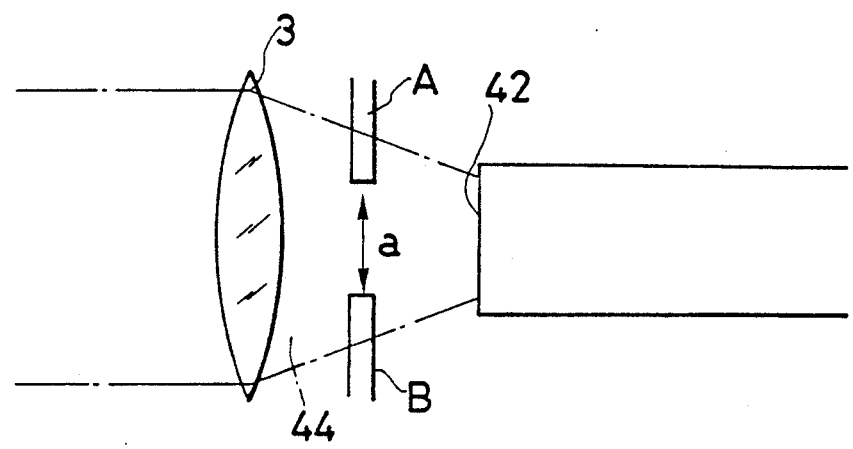
Figure 2A:
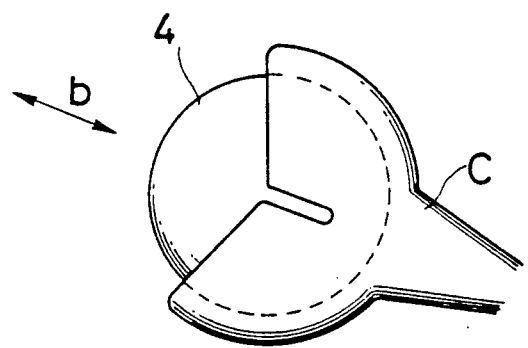
Figure 2B:
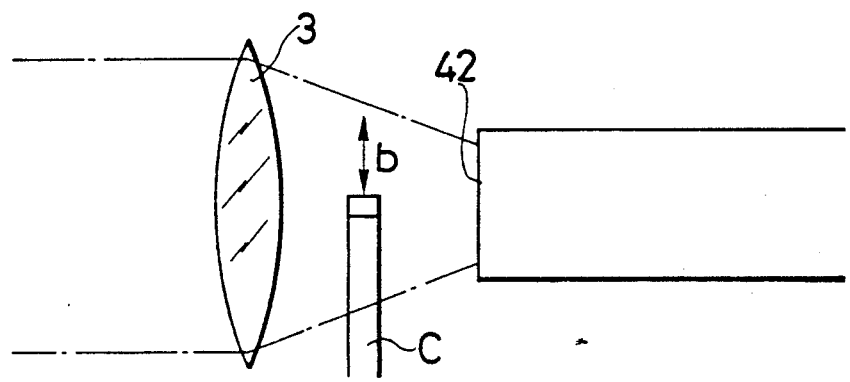
Figure 3:
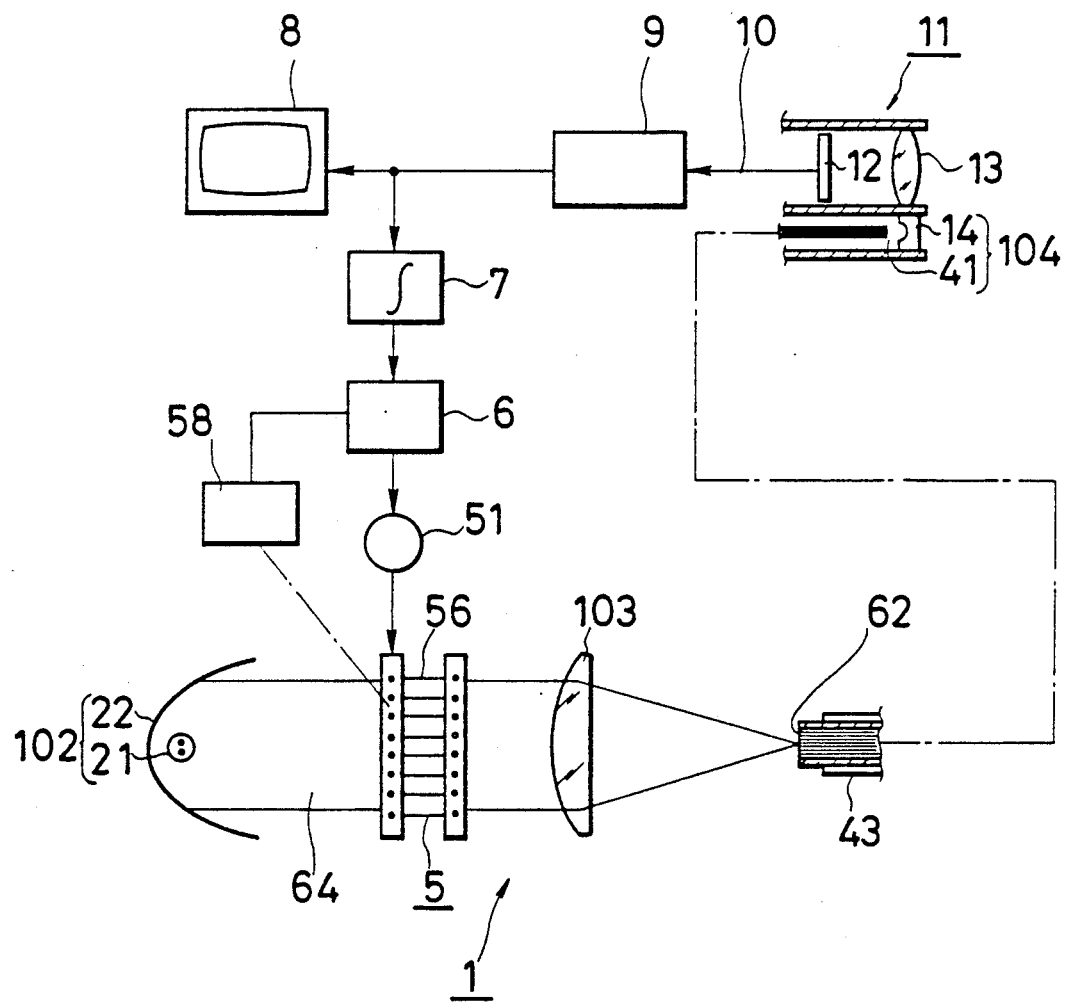
FIG. 3 is a view showing the constitution of an endoscope provided with a light source apparatus in the present invention.

As shown in FIG. 3, an endoscope using a light source apparatus of the present invention comprises a solid image pick-up element or CCD(charge coupled device) 12, an objective lens 13, a light guide 104 having an end tip 41, and an illuminating window 14, which are disposed in an end portion 11 inserted into a human's body. The CCD 12 is connected by a signal cable 10 to a monitor television 8 and an integral circuit 7 through a videoprocessor 9.

A light source apparatus 1 of the endoscope in the present invention comprises a light source 102 composed of a light source lamp 21 and a reflecting mirror 22, a condenser lens 103, and a light guide jack 43 for supporting a rear end 62 of the light guide 104. A light quantity adjusting device 5 has a plurality of throttle blades or fins 56 which can be opened and closed with respect to each other between the light source 102 and the condenser lens 103. A motor 51 for driving the light quantity adjusting device 5 is electrically connected to a motor driving circuit 6 and an integral circuit 7.

In the light source apparatus 1, light irradiated from the light source lamp 21 is reflected by the reflecting mirror 22 to generally form parallel light, and the parallel light is collected by the condenser lens 103 and is irradiated to the rear end 62 of the light guide 104. The quantity of the incident light irradiated to the rear end 62 of the light guide is uniformly adjusted by the light quantity adjusting device 5 as described later.

Figure 4:
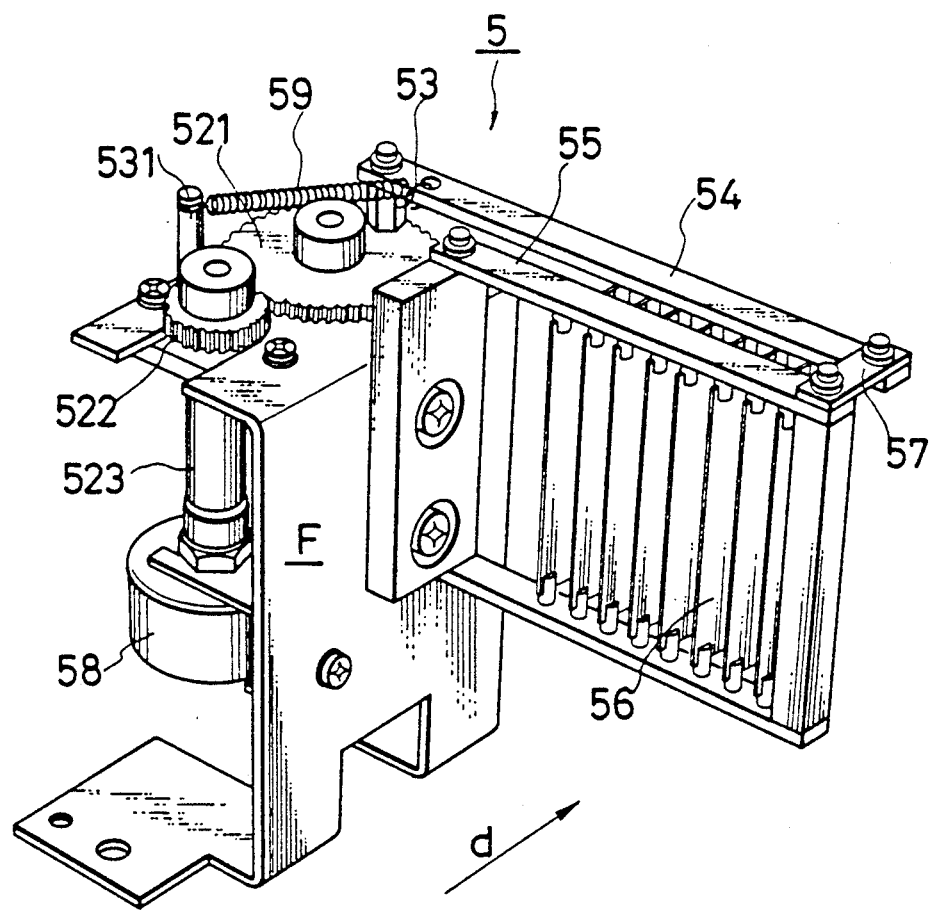
FIGS. 4 to 6 are perspective views showing a first embodiment of a device for adjusting light quantity in the light source apparatus of the endoscope in the present invention.
Figure 5:
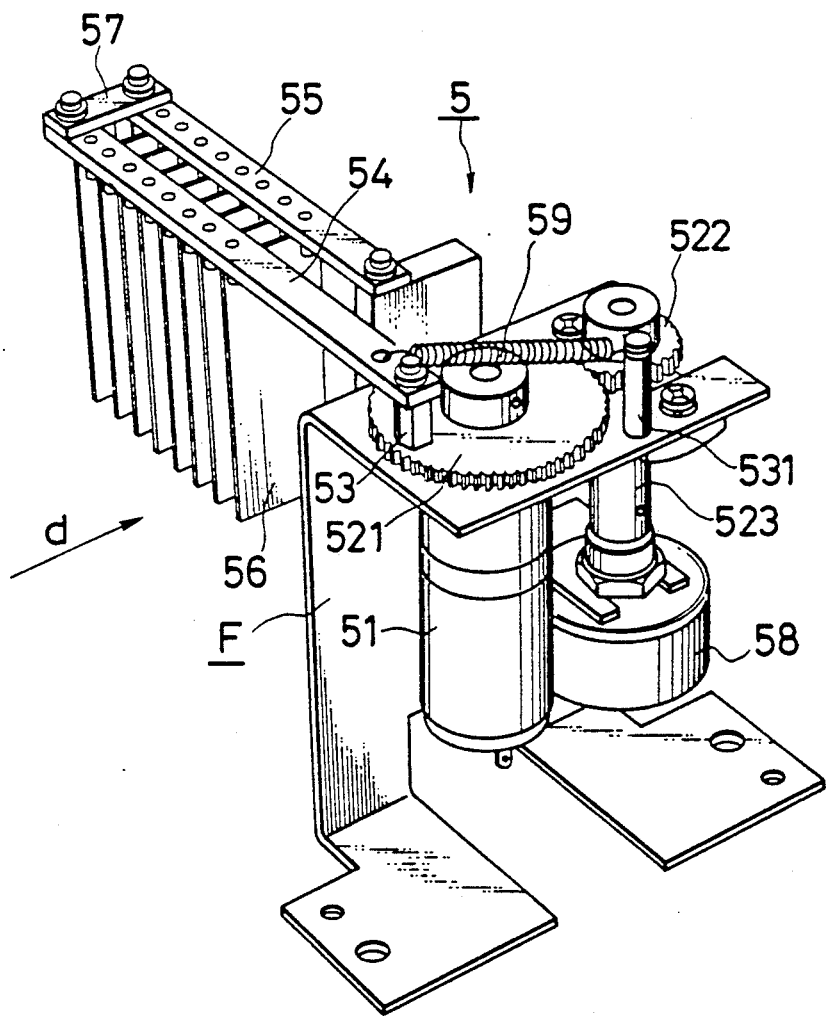
Figure 6:
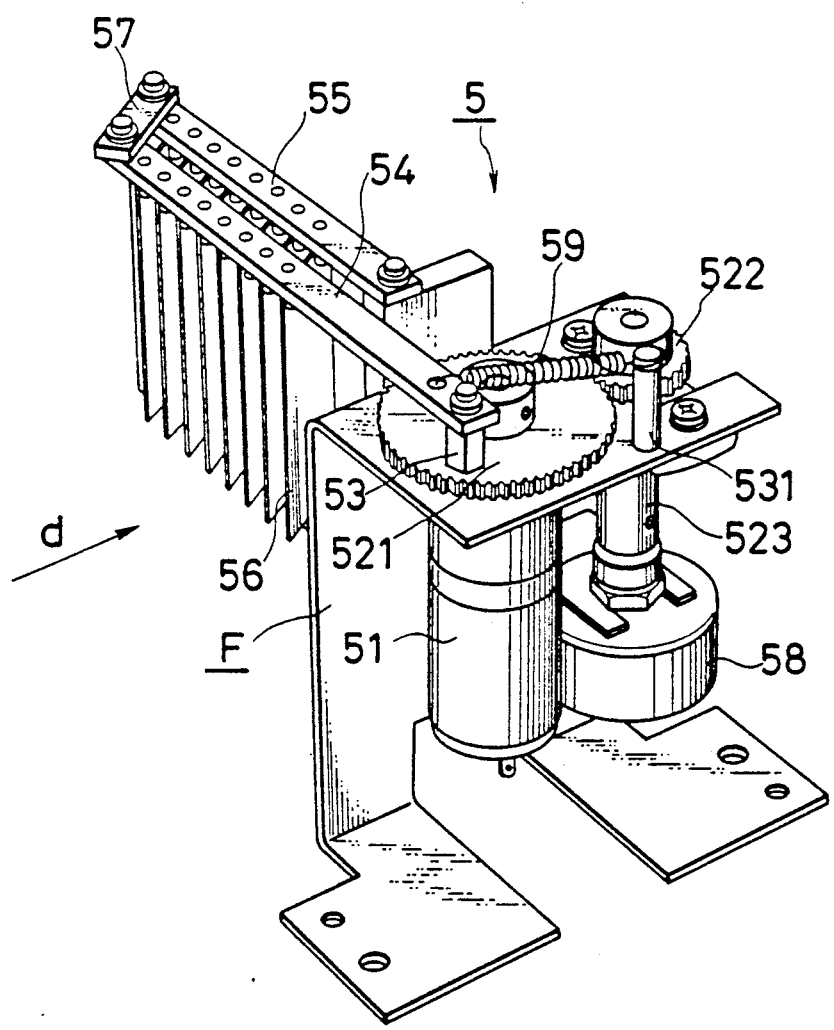

FIGS. 4 to 6 show a first embodiment of the light quantity adjusting device 5 in which a plurality of throttle blades or fins 56 are disposed in parallel to each other between a movable portion 54 and a stationary portion 55 connected to each other by a link 57. The other end of the movable portion 54 is connected to a stud 53 fixed to a gear 521 rotatably supported by a motor 51 as shown in FIGS. 5 and 6. The surfaces of the fins 56 are coated with a black coloring to prevent irregular reflection of light.

The stud 53 is connected to a pin 531 fixed to a frame F through a spring 59. The accuracy of sliding movement of the movable portion 54 can be further improved if the spring 59 is used.

The gear 521 is engaged with a gear 522 connected to a potentiometer 58 through a shaft 523.

The potentiometer 58 detects the open and closed positions of the fins 56, and transmits a detecting signal to the motor drive circuit 6 and the integral circuit 7 to display the adjusted situation of the illuminating intensity provided by the fins 56 on the monitor television or a panel at any time and to automatically control the open and closed positions of the fins 56.

In FIGS. 4 and 5, the light from the light source lamp 21 is transmitted to the rear end 62 of the light guide 104 through slits formed by the fins 56 in the direction of arrow d. When all of the fins 56 are perpendicular to the longitudinal direction of the elongated stationary portion 55 and the slits formed between the fins 56 are completely opened, the illuminating intensity of the light transmitted to the rear end 62 of the light guide is in the maximum state in which the output of the light source lamp 21 is constant.

When the integral circuit 7 detects an excessive illuminating intensity of the illuminated body, the integral circuit 7 transmits a starting signal for rotating the motor 51 to the motor drive circuit 6, and the motor 51 is thereby driven to rotate the gear 521.

Accordingly, as shown in FIG. 6, the movable portion 54 connected to the stud 53 on the gear 521 is slid by the cooperation of the link 57 and the spring 59, and all of the fins 56 are moved in a direction in which the slits formed between the fins are closed, thereby uniformly reducing the illuminating intensity.

When the illuminating intensity is increased, the motor 51 is instructed to be rotated in the reverse direction so that the gear 521 is rotated in the reverse direction, and the movable portion 54 is slid in a direction reverse to the above-mentioned direction and all of the fins 56 are moved in a direction in which the slits formed by the fins are opened. Accordingly, the slits formed between the fins 56 are opened, and the quantity of light incident onto the rear end 62 of the light guide is uniformly increased.

Figure 7:
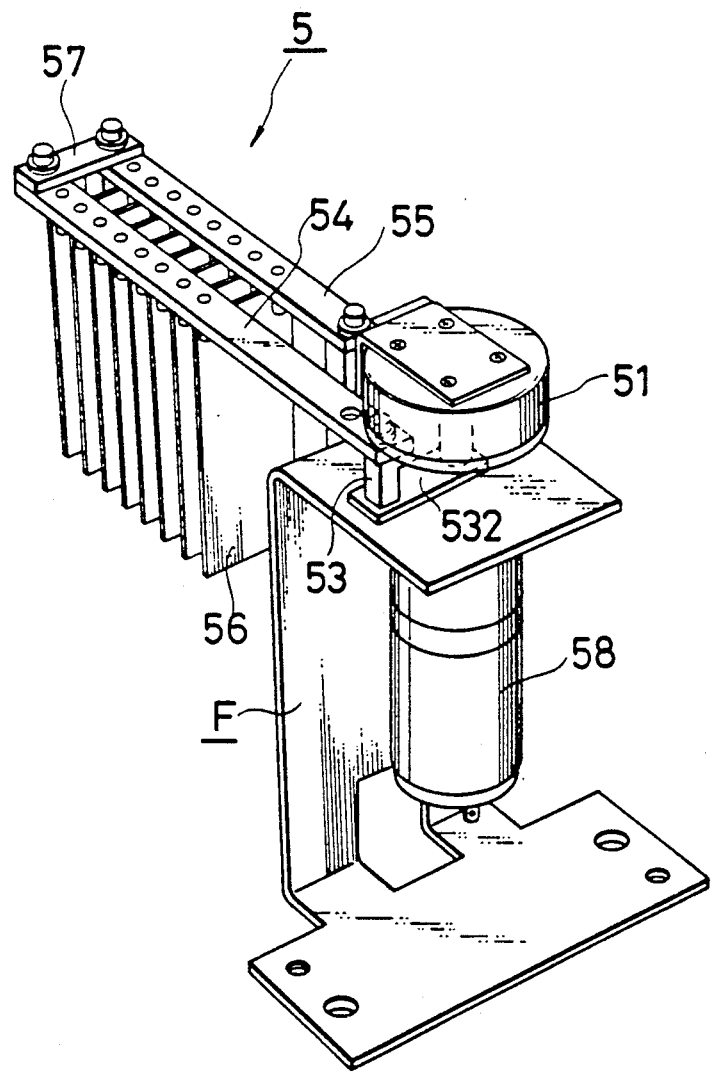
FIG. 7 is a perspective view showing a second embodiment of the light quantity adjusting device of the present invention.

FIG. 7 shows a light source apparatus in accordance with a second embodiment of the present invention in which a potentiometer 58 is directly connected to a motor 51 and a stud 53 for moving a movable portion 54 is linked to a sliding plate 532 connected to the motor 51, which is different from the construction of the first embodiment mentioned above. The other construction of FIG. 7 is similar to the one in the first embodiment.

In the second embodiment, similar to the first embodiment, slits formed between all of fins 56 can be opened and closed by the rotation of the motor 51 to adjust the illuminating intensity of an illuminated body, and further the apparatus can be made compact and light in comparison with the one in the first embodiment.

As a modified embodiment, a pulse motor may be rotatably connected to the movable portion 54, and the quantity of light may be adjusted by detecting the initial position of a motor shaft of the pulse motor by a photo coupler, etc., to move the movable portion 54. In such a modified embodiment, it is not necessary to dispose the potentiometer.

As described in detail in the embodiments mentioned above, in accordance with a light source apparatus in an endoscope of the present invention, a device for adjusting quantity of light comprises a plurality of throttle blades or fins disposed between a light source and a condenser lens and arranged in parallel to each other so as to open and close slits formed between the fins. A motor for moving the fins is driven by a signal from a motor drive circuit to adjust the open and closed angles of the fins, thereby facilitating the adjustment of the illuminating intensity of an illuminated body.

In the light source apparatus of the endoscope in the present invention, the quantity of light provided by the fins is adjusted by uniformly interrupting the quantity of the light incident onto the entire sectional region of a light guide, so that the distribution characteristics of the light irradiated onto the illuminated body are not prevented at all.

Accordingly, in the light source apparatus of the endoscope in the present invention, the illuminating intensity or brightness of the illuminated body can be adjusted without deteriorating the light distribution characteristics at all, thereby greatly improving observation accuracy of the illuminated body.

What is claimed is:

1. An endoscope apparatus, comprising:
a light source for generating light;
a lens means for collecting the light generated by the light source;
light guide means for receiving the light via the lens means; and,
light quantity adjusting means positioned between the light source and the lens means, for uniformly adjusting the quantity of the light conducted via the lens means to the light guide means independent of a throttled amount of light quantity, said light quantity adjusting means including;
a plurality of throttle blades opened and closed relative to each other so as to uniformly adjust the quantity of the light transmitted from the light source to the lens means via the adjusting means, and further including a stationary portion for supporting the throttle blades, and a movable portion connected to the stationary portion through a link for sliding the throttle blades with respect to the stationary portion, the opened and closed positions of the throttle blades being adjusted by sliding the movable portion.

2. An endoscope apparatus as claimed in claim 1, wherein said adjusting means comprises a plurality of throttle blades opened and closed relative to each other to adjust the quantity of light transmitted from the light source to the lens means.

3. An endoscope apparatus as claimed in claim 1, wherein a motor for sliding the movable portion is connected to a potentiometer for detecting the open and closed positions of the throttle blades.

4. An endoscope apparatus as claimed in claim 3, wherein the potentiometer is connected to the motor for sliding the movable portion through gear means.

5. An endoscope apparatus as claimed in claim 3, wherein the potentiometer is directly connected to a shaft of the motor for sliding the movable portion.

6. An endoscope apparatus as claimed in claim 1, wherein said adjusting means divides the light flux between the light source and the lens means into a plurality of striped light sources, and uniformly adjusts the quantity of light transmitted to the light guide means by interrupting each of the respective striped light sources simultaneously at the same ratio.

7. An endoscope apparatus, comprising:
a light source;
lens means for collecting light from the light source;
light guide means for receiving the light collected by the lens means; and
light quantity adjusting means disposed between the light source and the lens means for uniformly varying the amount of light guided to the light guide means while maintaining constant the intensity distribution of the light.

* * * * *